United States Patent
Costantino

(10) Patent No.: US 6,436,061 B1
(45) Date of Patent: Aug. 20, 2002

(54) ULTRASOUND TREATMENT OF VARICOSE VEINS

(76) Inventor: Peter D. Costantino, 12 Wright's Mill Rd., Armonk, NY (US) 10504

( * ) Notice: Subject to any disclaimer, the term of this patent is extended or adjusted under 35 U.S.C. 154(b) by 0 days.

(21) Appl. No.: 09/474,334

(22) Filed: Dec. 29, 1999

(51) Int. Cl.$^7$ .................................................. A61B 5/00
(52) U.S. Cl. .......................................... 601/2; 600/439
(58) Field of Search ..................... 601/2, 3, 4; 600/439, 600/371; 606/27, 28, 31; 607/96

(56) References Cited

U.S. PATENT DOCUMENTS

| | | | | |
|---|---|---|---|---|
| 5,108,359 A | * | 4/1992 | Granov et al. | 600/9 |
| 5,316,000 A | * | 5/1994 | Chapelon | 128/660.03 |
| 5,601,526 A | * | 2/1997 | Chapelon et al. | 601/3 |
| 5,656,015 A | * | 8/1997 | Young | 601/2 |
| 6,083,159 A | * | 7/2000 | Driscoll | 600/371 |
| 6,113,559 A | * | 9/2000 | Klopotek | 601/3 |

FOREIGN PATENT DOCUMENTS

FR 2672486 * 2/1991
FR 2672486 * 8/1992 ............ A61B/17/12

* cited by examiner

Primary Examiner—Marvin M. Lateef
Assistant Examiner—Eleni Mantis Mercader
(74) Attorney, Agent, or Firm—Michael G. Petit

(57) ABSTRACT

A method and apparatus for the non-invasive treatment of varicose veins. The vibrational energy in acoustic waves emanating from one or more source of ultrasonic energy is focused beneath the skin to cause localized heating and tissue disruption and/or destruction in and around the varicosed segment of the vein, particularly the venous endothelium. The localized tissue destruction is followed by localized fibrosis in and around the dilated portion of the varicosed vessel. The ultrasound-induced fibrosis includes thickening and loss of elasticity of the vascular wall. If a sufficiently high dosage of ultrasound energy is delivered to the vein, the varicosed portion of the vessel will be obliterated, providing a therapeutic result similar to that obtained by injection sclerotherapy or vein stripping. Alternatively, focused ultrasound may be used to induce fibrosis in the tissue overlying the varicosed vessel thereby providing a relatively inelastic barrier which resists unsightly deformation of the skin overlying the varicose vein due to venous dilation.

5 Claims, 2 Drawing Sheets

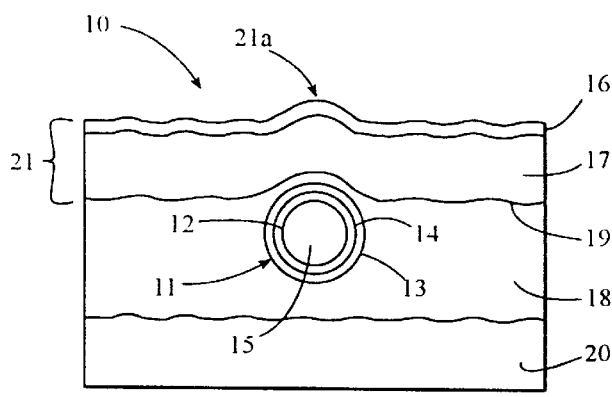
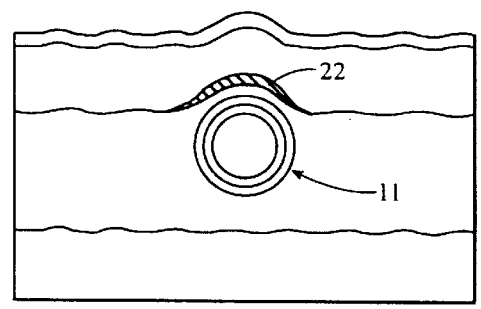
Figure 1
Figure 2
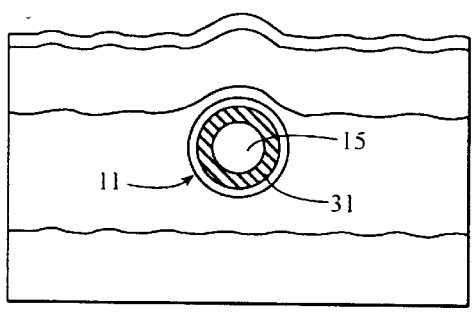
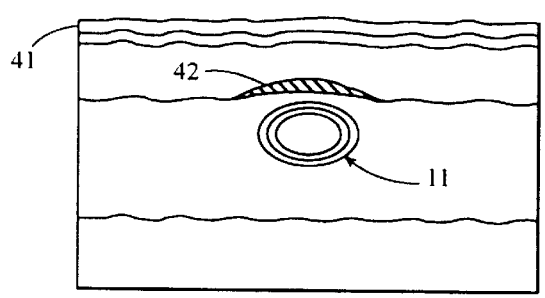
Figure 3
Figure 4
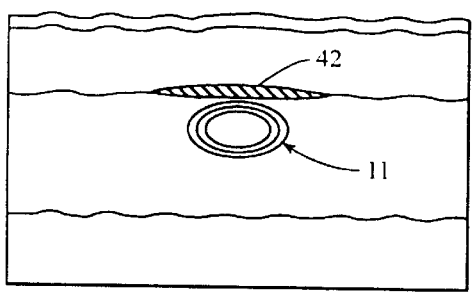
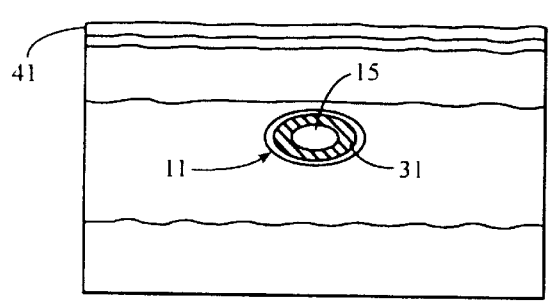
Figure 5
Figure 6

ULTRASOUND TREATMENT OF VARICOSE VEINS

BACKGROUND OF THE INVENTION

1. Field of the Invention

This invention relates to a method and apparatus for treating varicosed veins, and, more particularly, to a method for treating varicose veins by the non-invasive administration of ultrasound therapy.

2. Prior Art

Varicose veins include superficial, tortuous veins, usually in the lower extremities, which have become dilated. The most common cause of varicose veins is attributed to vascular valve dysfunction wherein one or more of the valves in the effected vein fail to prevent blood from flowing backward, away from the heart. The failure of the venous valves, together with the force of gravity, permits blood to pool within the vessel with concomitant dilation thereof While recent studies suggest that inherent weakness of the venous wall is a factor, if not the major factor, causing venous distention and associated varicosity, varicose veins remain an irreversible disease at this time. Whatever the cause of varicose veins, the dilated vessel may protrude outwardly into the soft subcutaneous and cutaneous tissue overlying the vessel to visibly deform the overlying skin.

The conservative symptomatic treatment of varicose veins includes the occasional application of a loose tourniquet around the upper thigh or, more usually, the application of a compressive wrap to the effected extremity and/or the periodic elevation thereof While conservative treatment is effective for relieving the discomfort associated with varicose veins, it neither corrects the condition nor provides an acceptable cosmetic result. As mentioned above, a varicose vein is generally regarded as an irreversible disease at the present time. Accordingly, methods such as sclerotherapy have been developed for diverting venous blood from the superficial varicosed vein to a deeper vein. Sclerotherapy is administered by injecting a chemical into the vein which damages the intimal lining thereof and inducing fibrosis. The progressive fibrosis eventually occludes the lumen of the varicosed vessel. In a most invasive procedure, the varicosed portion of vein is surgically removed by ligation and stripping.

While conservative treatment of varicose veins will, in some instances, provide symptomatic relief, it will not correct the underlying problem. Less conservative invasive methods such as sclerotherapy or vein stripping result in total destruction of the varicosed portion of the vein as well as non-varicosed portions. Thus, at the present time there remains a continuing need for an effective, minimally invasive method for treating varicose veins.

SUMMARY OF THE INVENTION

It is a first object of the present invention to provide a minimally invasive method for treating varicose veins.

It is a further object of the invention to provide a method for reducing the visible deformation of skin due to the dilation of varicose veins.

It is yet another object of the invention to provide a method for reinforcing the wall of a varicosed portion of a vein thereby reducing dilation thereof.

It is still another object of the invention to provide a noninvasive method for inducing the formation of a blood clot within a varicosed vein thereby reducing or preventing the flow of blood through the varicosed vein.

It is another object of the invention to provide a non-invasive means for disrupting the venous endothelium thereby inducing sclerosis of the wall of the vein.

It is also an objective of this invention to provide an ultrasound delivery apparatus which may be used in accordance with the present method to accomplish the foregoing objects of the invention The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

BRIEF DESCRIPTION OF THE DRAWINGS

FIG. 1 is a cross-sectional transverse view of a tissue section containing a superficial varicosed vein, viewed in the direction of venous blood return.

FIG. 2 is a cross-sectional transverse view of the tissue section as in FIG. 1 after a extravascular lesion is formed by damaging the extravascular tissue adjacent to the vein and/or the venous endothelium with focused ultrasonic energy.

FIG. 3 is a cross-sectional transverse view of the tissue section as in FIG. 1 after an intravascular lesion is formed by damaging the muscular middle layer and/or the endothelial tissue lining the inner wall of the vein with focused ultrasonic energy.

FIG. 4 is a is a cross-sectional view of the tissue section in accordance with FIG. 2 wherein the tissue section bearing the lesion is compressed by the external application of a compression bandage.

FIG. 5 is a cross-sectional view of a section of tissue in accordance with FIGS. 1, 2 and 4 after the compression bandage is removed, illustrating how the reinforcing scaffolding formed in response to the extravascular tissue damage, overlies the varicosed vein, reducing the flow of blood therethrough and constraining the dilation and outward protrusion of the varicosed vein.

FIG. 6 is a is a cross-sectional view of the tissue section in accordance with FIG. 3 wherein the tissue section bearing the lesion is compressed by the external application of a compression bandage.

DESCRIPTION OF THE PREFERRED EMBODIMENTS

Figure 7:
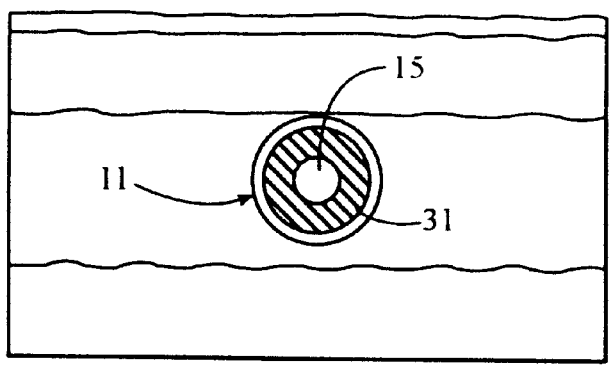
FIG. 7 is a cross-sectional view in accordance with FIG. 3 after the compression bandage is removed illustrating how the ultrasonic ablation of vascular tissue induces intravascular fibrosis which eventually thickens the wall of the vein resulting in either partial or total occlusion of the lumen within the varicosed vein thereby diverting venous blood return to a perforated vein and relieving pressure on the vascular wall.

With reference to FIG. 1, a portion of superficial tissue 10, which includes a varicose vein 11 passing therethrough, is shown in transverse cross-section with respect to the direction of blood flow through the varicose vein 11. The varicosed vein 11 comprises three coaxial layers or "coats" of tissue: the endothelial inner layer 12, a outer layer 13 and a middle layer 14 interposed between the inner layer 12 and outer layer 13. A fourth, very thin elastic layer (not shown) separates the inner layer 12 from the middle layer 14. The outer layer 13 is comprised principally of elastically deformable connective tissue, while the inner layer 12 comprises principally endothelium. The middle layer 14, which is comprised of muscle cells, is relatively weak; for example, weaker than the corresponding layer in an artery, and, for this reason, a vein readily dilates in response to increased pressure within the venous lumen 15.

The sectioned tissue 10 includes skin 21 comprised of a epidermal layer 16 and the underlying dermis 17. The subcutaneous tissue layer 18 is separated from the dermis by a layer of connective tissue 19. A band of muscle 20 is shown underlying the varicose vein 11. A portion of the skin 21, indicated at numeral 21 a, overlying the varicose vein is deformed outwardly with respect to the surrounding skin 21, the deformation being visible to the unaided eye and cosmetically undesirable.

FIG. 2 is a cross-sectional elevational view of the tissue section 10 of FIG. 1 after a extravascular lesion 22 is formed by damaging extravascular tissue overlying the vein with focused ultrasonic energy. Subsequent to ultrasonically traumatizing tissue overlying the vein 11, the body's normal inflammatory response to the damage includes progressive fibrosis in the affected area with the formation of a relatively inelastic, fibrous layer of connective tissue. If, following lesion formation, a compression bandage 41 (FIG. 4) is applied to the portion of skin 21 a overlying the vein 11, the progressive formation of the fibrous layer 42 can be constrained to develop within a plane substantially parallel to the skin surface. When the inflammatory response has subsided and the fibrous layer 41 is fully developed, the compression bandage 41 is removed as shown in FIG. 5. The fibrous layer 42 forms a inelastic barrier preventing deformation of the skin in response to dilation of the vein 11.

While the forgoing approach may provide a preferred cosmetic effect insofar as skin deformation is concerned, such a fibrous layer will not prevent further dilation of the varicose vein 11 directed inwardly and associated discomfort. FIG. 3 is a cross-sectional transverse view of the tissue section as in FIG. 1 illustrating an intravascular lesion 31 formed by damaging the muscle cells comprising the vein's middle layer 14 and the endothelial tissue of the vein's inner layer 12 with focused ultrasonic energy. The sequellae to such intravenous damage includes fibrosis, wall thickening, with a concomitant reduction in the elasticity of the vein and constriction of the venous lumen 15. If, subsequent to lesion formation, a compression bandage 41 is applied to the portion of the skin overlying the lesion 31, as shown in FIG. 6, then removed, as shown in FIG. 7, the varicosed vein 11 will have both a strengthened (less elastic) wall and a smaller lumen diameter.

In practice, when using ultrasound to treat varicose veins in accordance with the method of the present invention, it is preferable to administer focused ultrasound energy to the varicosed vein in its entirety. The focused ultrasound is delivered to the vein in a dose sufficient to cause disruption of the venous endothelium therein. The targeted portion of the vein (i.e.: the portion of the varicosed vein receiving focused ultrasound treatment) is then compressed by means of a compression bandage. As the damaged endothelium heals, it is accompanied by a proliferation of cellular tissue which at least partially occludes the venous lumen thereby reducing or eliminating blood flow therethrough, and dilation thereof. If the endothelium is sufficiently damaged during treatment, the endothelial tissue may fuse, causing total obstruction of the venous lumen.

Figure 8:
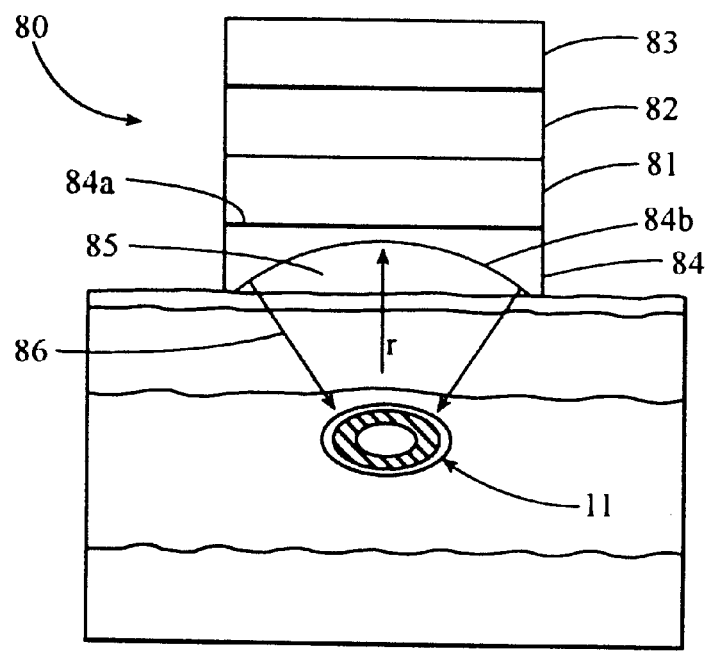
FIG. 8 is an elevational plan view of a ultrasound delivery apparatus in accordance with the present invention which may be used to deliver focused ultrasonic vibrational energy on a portion of subcutaneous, intravascular or extravascular tissue in order to induce fibrosis therein.

FIG. 8 is an elevational plan view of a ultrasound delivery apparatus 80 in accordance with the present invention which may be used to deliver focused ultrasonic vibrational energy to impinge upon a targeted portion of subcutaneous, intravascular or extravascular tissue in order to ablate the targeted tissue and/or induce fibrosis therein. A ultrasonic transducer 81 is in electrical communication with a ultrasonic generator 82. The ultrasonic generator 81 is operable for providing a electrical output signal having a frequency between 1 megahertz and 100 megahertz, and most preferably around 25 megahertz. The ultrasonic transducer element 81, which is preferably a piezoelectric crystalline material or a electrostrictive device, receives the electrical output signal from the generator 82 and produces mechanical vibrations having a frequency which is synchronous with the electrical output signal. The ultrasonic generator 82 is energized by means of a power source 83.

The ultrasonic transducer 81 is in vibrational communication with a first side 84a of a focusing element 84, The focusing element has a concave second side 84b which is in vibrational communication with the tissue overlying and including the varicose vein. A layer of an impedance matching material 85, such as a fluid or a gel, wherein the velocity of ultrasound therein is similar to the velocity of the ultrasound in body tissue at the operating frequency, may be interposed between the concave second surface 84b of the ultrasonic transducer and the epidermis 16 to optimize power delivery to the targeted tissue. The radius of curvature of the concave second surface 84b is most preferably equal to the distance r between the concave second surface and the tissue targeted for destruction 11.

With reference now to FIG. 8, in order to determine a value for r, it is necessary to determine the depth d of the varicosed vein below the skin surface. Thus, an imaging device operable for determining the position of the varicosed vein, is preferably incorporated into, and integral with, the device containing the source of treatment ultrasound. A suitable imaging device is provided by a device comprising a source of imaging ultrasound energy, a detector for imaging ultrasound energy and a computer means. Ultrasound imaging is widely used for visualizing soft tissue. An example of an ultrasound treatment and imaging device, which may be adapted for use with the method of the present invention, is disclosed, for example, by Watkins et al. in U.S. Pat. No. 5,769,790, the contents of which is incorporated herein by reference thereto. The visualization of a varicose vein generally employs pulsed-echo techniques wherein an image is computer generated, in real time, from measurements of the amplitude of the envelope of echo signals at a receiver disposed at a known position with respect to the source of imaging ultrasound. Alternatively, the depth d of a varicosed vein beneath the surface of the skin overlying the varicosed vein may be obtained by measuring the time interval between the time a ultrasound pulse is delivered to tissue containing the varicosed vein, and the time a Doppler-shifted echo of the pulse is detected by a receiver. If the velocity of the imaging ultrasound in tissue is known, the measured time interval, together with geometric considerations, can be used to compute the depth, or distance d, of the vessel beneath the skin surface.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What I claim is:

1. A method for treating a varicose vein underlying a portion of skin on the body of a patient comprising the steps of:
   (a) presenting a source of focused ultrasonic vibrational energy; then
   (b) placing the source of ultrasonic vibrational energy in vibrational communication with the portion of skin overlying the varicose vein; then
   (c) focusing at least a portion of the ultrasonic vibrational energy produced by the source of ultrasonic vibrational energy to impinge upon target tissue overlying the varicose vein and disposed between the overlying skin and the varicose vein wherein the target tissue does not comprise the varicose vein; then
   (d) continuing step (c) until sufficient target tissue is damaged to induce the formation of a layer of fibrous tissue between the varicose vein and the portion of skin overlying the varicose vein without causing substantial damage to tissue comprising the varicose vein.

2. The method of treating a varicose vein in accordance with claim 1 wherein the source of ultrasonic vibrational energy operates at a frequency between one megahertz and 100 megahertz.

3. The method of claim 1 wherein the source of ultrasonic vibrational energy comprises an ultrasonic generator providing an electrical output signal, and a ultrasonic transducer operable for receiving the electrical output signal and producing a mechanical vibration output in response to receiving the electrical output signal, wherein the mechanical vibration is synchronous with the electrical output signal.

4. The method of claim 3 further comprising a focusing element having a first side adapted to receive the mechanical vibration output from the transducer and a concave second side in opposition to the first side.

5. The method of claim 4 wherein when the concave second side is in mechanical communication with the portion of skin overlying the varicose vein in accordance with step (b), the concave second side has a radius of curvature substantially equal to the distance between the concave second side of the focusing element and tissue overlying the varicose vein.

* * * * *